(12) United States Patent
Lee

(10) Patent No.: US 11,617,574 B2
(45) Date of Patent: Apr. 4, 2023

(54) METHOD FOR MANUFACTURING GOLD THREAD WITH NO DRAWING-INDUCED INCONSISTENCY, AND GOLD THREAD MANUFACTURED BY SAME

(71) Applicant: Jeong Hyeon Lee, Seoul (KR)

(72) Inventor: Jeong Hyeon Lee, Seoul (KR)

(*) Notice: Subject to any disclaimer, the term of this patent is extended or adjusted under 35 U.S.C. 154(b) by 793 days.

(21) Appl. No.: 16/485,742

(22) PCT Filed: Feb. 7, 2018

(86) PCT No.: PCT/KR2018/001649
§ 371 (c)(1),
(2) Date: Aug. 13, 2019

(87) PCT Pub. No.: WO2018/147634
PCT Pub. Date: Aug. 16, 2018

(65) Prior Publication Data
US 2020/0000467 A1    Jan. 2, 2020

(30) Foreign Application Priority Data

Feb. 13, 2017  (KR) .................. 10-2017-0019566

(51) Int. Cl.
*A61B 17/06*     (2006.01)
*D02G 3/44*      (2006.01)
*A61L 17/04*     (2006.01)
*D02G 3/12*      (2006.01)
(Continued)

(52) U.S. Cl.
CPC ........ *A61B 17/06166* (2013.01); *A61L 17/04* (2013.01); *D02G 3/448* (2013.01); *D02G 3/12* (2013.01); *D02G 3/28* (2013.01); *D02G 3/36* (2013.01)

(58) Field of Classification Search
CPC .. D02G 3/12; D02G 3/28; D02G 3/36; D02G 3/448; A61B 17/06166; A61L 17/04
See application file for complete search history.

(56) References Cited

U.S. PATENT DOCUMENTS 2,963,850 A * 12/1960 Rosenblatt ................ D01F 9/08
57/259
2004/0267315 A1* 12/2004 Wolf ....................... A61L 17/06
606/230
(Continued)

FOREIGN PATENT DOCUMENTS

CN       202530226 U   11/2012
KR       10-1450454 B1 10/2014
(Continued)

OTHER PUBLICATIONS

Translation of KR101450454B1, retrieved May 31, 2022.*

*Primary Examiner* — Shaun R Hurley

(57) ABSTRACT

A method for manufacturing a gold thread by spirally twisting together a plurality of gold rods. The method comprises passing a gold drawing material through a die aperture to form gold rods. Winding at least two of the gold rods on at least two gold rod receiving rollers. Receiving the gold rods from the receiving rollers and twisting the gold rods to form a gold thread. Winding the gold thread on a gold thread receiving roller and supplying the gold thread from the gold thread receiving roller to a cutter and cutting the gold thread into a certain length.

3 Claims, 4 Drawing Sheets

(51) Int. Cl.
*D02G 3/28* (2006.01)
*D02G 3/36* (2006.01)

(56) References Cited

U.S. PATENT DOCUMENTS

| | | | | |
|---|---|---|---|---|
| 2005/0288775 | A1* | 12/2005 | Dong | A61L 27/446 623/23.74 |
| 2008/0046094 | A1* | 2/2008 | Han | A61F 2/0059 623/23.72 |
| 2009/0142275 | A1* | 6/2009 | Phillips | A61K 49/0021 424/9.1 |

FOREIGN PATENT DOCUMENTS

| | | | | |
|---|---|---|---|---|
| KR | 10-2015-0137727 A | 12/2015 | | |
| KR | 10-1585112 B1 | 1/2016 | | |
| KR | 10-1651542 B1 | 8/2016 | | |
| KR | 10-2016-0131634 A | 11/2016 | | |
| KR | 20160131853 A | * 11/2016 | | B21C 1/16 |

* cited by examiner

METHOD FOR MANUFACTURING GOLD THREAD WITH NO DRAWING-INDUCED INCONSISTENCY, AND GOLD THREAD MANUFACTURED BY SAME

CROSS-REFERENCE TO PRIOR APPLICATIONS

This application is a national Stage Patent Application of PCT International Patent Application No. PCT/KR2018/001649, filed on Feb. 7, 2018 under 35 U.S.C. § 371, which claims priority of Korean Patent Application No. 10-2017-0019566, filed on Feb. 13, 2017, which are all hereby incorporated by reference in their entirety.

TECHNICAL FIELD

The present invention relates to a method of manufacturing a gold thread, and more particularly, to a method of manufacturing a gold thread without drawing-induced inconsistency and a gold thread manufactured by the same method, which can secure enough rigidity by being relatively thinner than the thickness of typical gold rods and spirally twisting a plurality of gold rods.

BACKGROUND ART

In general, non-surgical procedures are generally being used in cosmetic surgery or plastic surgery which is performed to improve an affected part or to correct a partially damaged part of a human body, instead of surgical procedures.

The non-surgical procedures include non-surgical cosmetic procedures using fillers and non-surgical lifting procedures which are wrinkle removal and skin sagging prevention procedures using sutures. Since sutures formed of synthetic resins used for lifting procedures are decomposed in the body after a certain period of time, periodic retreatment is needed. Also, since side effects may occur in the human body, a thread formed of gold that can prevent the side effects occurring in the human body is being used in recent years.

As a method for manufacturing the gold thread, Korean Patent No. 10-1450454 discloses "manufacturing apparatus and manufacturing method of gold thread using artificial plastic surgery". In this patent, a gold rod having the same diameter as the aperture of a die is formed while passing a drawing material formed of gold through the diameter of the die. The gold rod is heated and cooled, and then is cut and compressively rolled to manufacture a gold thread having a certain length.

a. However, in this registered patent, since the balance of force for passing the diameter of the die is not equal in the process of drawing in a single line so as to have the same diameter as the aperture of the die while passing through the diameter of the die, the gold rod is bent and rolled to one side. Accordingly, since bending deformation and fracture occur in the cut gold rod when cutting the gold rod, the defective rate increases. Also, since the working time through the compression-rolling process for straightening the bending deformation increases, the productivity is reduced.

In addition, since the contact area with the skin is narrow, the skin wrinkle improvement, moisturizing effect and antibacterial properties are deteriorated when using the gold thread.

(Patent Document 1) Korean Patent No. 10-1450454

DISCLOSURE

Technical Problem

The present invention provides a method of manufacturing a gold thread without drawing-induced inconsistency and a gold thread manufactured by the same method, which can secure enough rigidity by being relatively thinner than the thickness of typical gold rods and spirally twisting a plurality of gold rods.

The present invention also provides a method of manufacturing a gold thread without drawing-induced inconsistency and a gold thread manufactured by the same method, which can increase the skin anti-aging and antibacterial effect by spirally twisting a plurality of gold rods to form a gold thread and thus increasing the frictional force through a wider surface area than a gold thread of the same diameter.

Technical Solution

In one general aspect, a method of manufacturing a gold thread without drawing-induced inconsistency includes:
drawing a gold rod having the same diameter and shape as the aperture of a die while passing a drawing material formed of gold through a die aperture having a diameter of 0.02 mm or less and winding the gold rod on a roller;
receiving two strands of gold rod wound on the roller and twisting the two strands of gold rod;
winding a gold thread twisted with the two strands of gold rod on a roller; and
cutting the gold thread wound on the roller into a certain length, wherein the gold thread cut in the cutting of the gold thread is not bent by twisting the two strands of gold rods.

The gold thread may be twisted with three strands of gold rod.

Other features and aspects will be apparent from the following detailed description, the drawings, and the claims.

Advantageous Effects

According to an embodiment of the present invention, since enough rigidity can be secured by being relatively thinner than the thickness of typical gold rods and spirally twisting a plurality of gold rods, the bending property due to drawing can be improved, and the accuracy can be increased. Accordingly, the defective rate is reduced and thus the productivity can be improved.

In addition, by forming a gold thread by twisting a plurality of gold rods spirally, as the surface area increases compared to gold threads of the same diameter, the frictional force with the skin is increased, and the lifting effect of pulling the skin can be enhanced. Also, the pharmacological action of gold can be promoted to improve skin aging, cell regeneration and growth, regeneration of damaged tissues. In addition, antibacterial property can be increased to prevent occurrence of side effects.

BEST MODE

Figure 1:
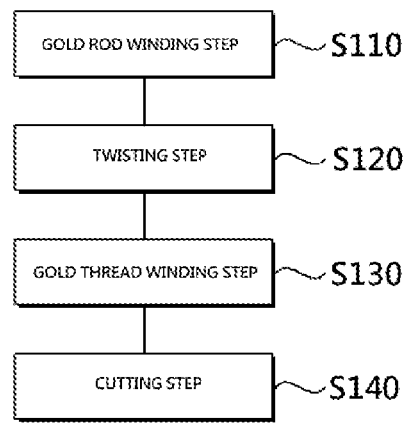
FIG. 1 is a flowchart illustrating a method of manufacturing a gold thread according to an embodiment of the present invention.

Hereinafter, exemplary embodiments of the present invention will be described in detail with reference to the accompanying drawings such that those skilled in the art can easily implement the present invention. However, the present invention can be implemented in various forms, and is not limited to embodiments described in this disclosure. Like parts are designated by like reference numerals throughout the specification.

Figure 2:
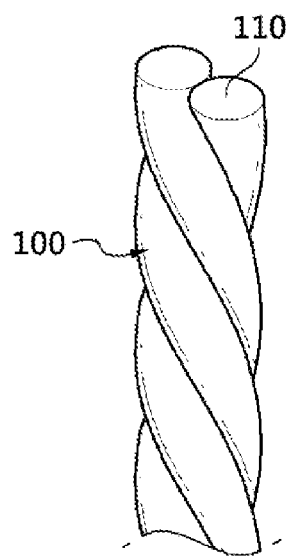
FIGS. 2 to 3 are perspective views illustrating gold threads according to an embodiment of the present invention.
Figure 3:
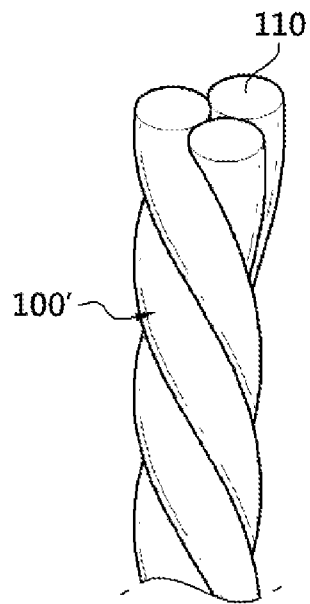

FIG. 1 is a flowchart illustrating a method of manufacturing a gold thread according to an embodiment of the present invention. FIGS. 2 to 3 are perspective views illustrating gold threads according to an embodiment of the present invention.

Referring to FIG. 1, a method of manufacturing a gold thread without drawing-induced inconsistency according to an embodiment of the present invention includes drawing a gold rod and winding the gold rod on a roller S110, receiving a plurality of gold rods wound on the roller in operation S110 and twisting the plurality of gold rods S120, winding a gold thread twisted with the plurality of gold rods on a roller in operation S130, and cutting the gold thread wound on the roller in operation S130 into a certain length S140.

A process of manufacturing a gold thread used for a subject who undergoes plastic (cosmetic) procedure or surgery using a gold thread having malleability by forming a gold rod having a diameter of 0.02 mm or less and spirally twisting the gold rod will be described in detail with reference to the above processes.

In operation S110, a god rod having the same diameter and shape as the aperture of a die while passing a drawing material formed of gold through a penetrated aperture of the die. The diameter of the aperture may be about 0.02 mm or less.

At least two of dies may be consecutively disposed such that the diameter gradually decreases. Thus, the diameter of the gold rod is sequentially reduced, and the diameter finally becomes 0.02 mm or less. The gold rod 110 projecting from the aperture of the die is wound on a roller.

In operation S120, the plurality of gold rods 110 wound on the roller in operation S110 are supplied to be twisted. A gold thread 100 may be formed by spirally twisting two strands of gold rod while rotating a gold rod supplied from one roller about a gold rod supplied from the other roller as shown in FIG. 2. By using this method, a gold thread 100' twisted with three strands of gold rods may be formed as shown in FIG. 3. The method of twisting the gold threads may be a typical method applied to the textile technology.

In operation S130, the gold threads 100 and 100' twisted with the plurality of gold rods in operation S120 are wound on the rollers.

In operation S140, the gold thread twisted with the plurality of gold rods and wound on the roller in operation S130 is cut into to a certain length by a cutter. The cutter may be an apparatus that can finely cut the gold thread into a length of about 3 cm to about 7 cm.

If the gold thread is cut to 3 cm or less, the procedure and surgery through the syringe is difficult, and if the length exceeds about 7 cm, it is difficult to work due to too long length.

Since the gold thread cut in operation S140 is twisted with a plurality of gold rods, the density difference between the both ends of the gold rod corresponding to each other in the direction orthogonal to the length direction of the gold rod is offset and thus the gold thread is not bent, thereby improving the flexibility due to the drawing of the gold rod. Thus, the productivity can be improved by removing a work process for straightening the gold thread. Also, since the gold thread can maintain the thread shape of about 0.04 mm even if two or three strands of gold rod having a diameter of about 0.02 mm are spirally twisted, the gold thread can be applied to medical procedures and surgery.

Figure 4:
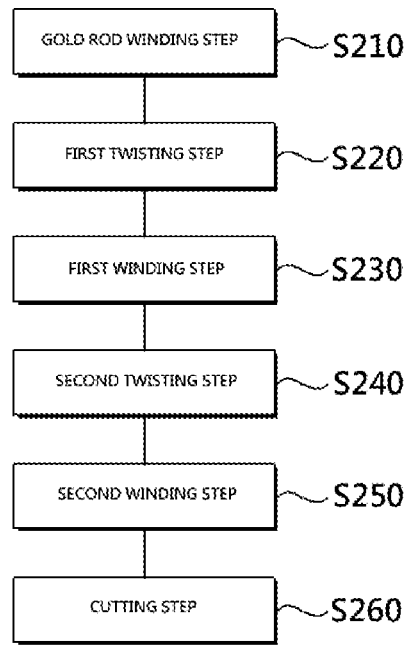
FIG. 4 is a flowchart illustrating a method of manufacturing a gold thread according to another embodiment of the present invention.
Figure 5:
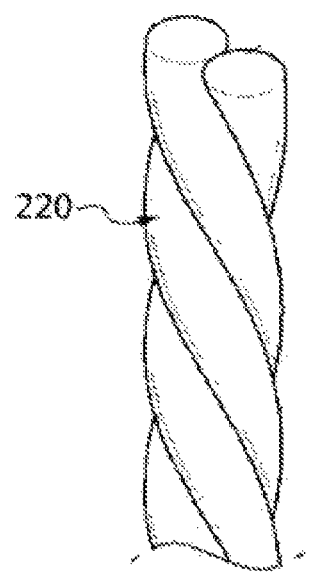
FIGS. 5 to 6 are perspective views illustrating gold threads according to another embodiment of the present invention.
Figure 6:
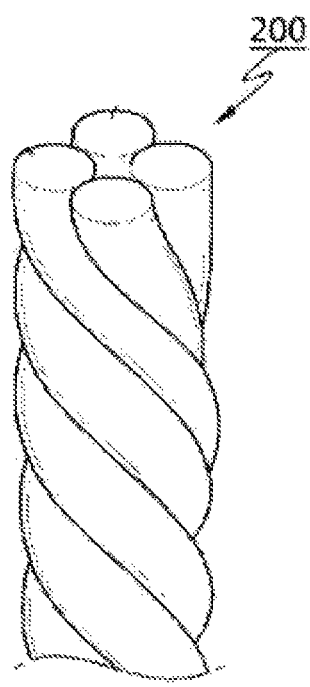

FIG. 4 is a flowchart illustrating a method of manufacturing a gold thread according to another embodiment of the present invention. FIG. 5 is a perspective view illustrating a gold thread according to another embodiment of the present invention.

Referring to FIG. 4, a method of manufacturing a gold thread without drawing-induced inconsistency according to another embodiment of the present invention includes drawing a gold rod and winding the gold rod on a roller S210, receiving two strands of gold rod wound on each of the rollers and twisting the two strands of gold rod S220, winding a gold thread twisted with the two strands of gold rod on a roller S230, receiving the gold threads wound on each of the rollers and twisted with the two strands of gold rod and twisting the gold threads S240, winding the gold thread twisted with the four strands of gold rod on a roller, and cutting the gold thread wound on the roller and twisted with the four strands of gold rod into a certain length S260.

a. A process of manufacturing a gold thread used for a subject who undergoes plastic (cosmetic) procedure or surgery using a gold thread by spirally twisting two strands of gold rod having a diameter of 0.02 mm or less to form a gold thread twisted with the two strands of gold rod and then by spirally twisting the gold threads again to form a gold thread having four strands of gold rod will be described in detail with reference to the above processes.

In operation S210, a god rod having the same diameter and shape as the aperture of a die while passing a drawing material formed of gold through a penetrated aperture of the die. The diameter of the aperture may be about 0.02 mm or less.

At least two of dies may be consecutively disposed such that the diameter gradually decreases. Thus, the diameter of the gold rod is sequentially reduced, and the diameter finally becomes 0.02 mm or less. The gold rod 110 projecting from the aperture of the die is wound on a roller.

In operation S220, two strands of gold rod wound on each of the rollers in operation S210 are each supplied and twisted. A gold thread 220 twisted with two strands of gold rod may be formed by spirally twisting two strands of gold rod while rotating a gold rod supplied from one roller about a gold rod supplied from the other roller as shown in FIG. 5. The method of twisting the gold thread twisted with two strands of gold rod may be a typical method applied to the textile technology.

In operation S230, the gold thread twisted with two strands of gold rods twisted with two gold rods in operation S220 is wound on a roller.

In operation S240, the gold threads twisted with two strands of gold rod wound on each of the rollers in operation S230 are each supplied and twisted. A gold thread 200 twisted with four strands of gold rod may be formed by rotating a gold thread twisted with two strands of gold rod supplied from one roller about a gold thread twisted with two strands of gold rod supplied from the other roller as shown in FIG. 5. The method of twisting the gold thread twisted with four strands of gold rod may be a typical method applied to the textile technology.

In operation S250, the gold thread twisted with four strands of gold rod by twisting the gold threads twisted with two strands of gold rod in operation S240 is wound on a roller.

In operation S260, the gold thread twisted with four strands of gold rod by twisting the gold threads twisted with two strands of gold rod and wound on the roller in operation S240 is cut into to a certain length by a cutter. The cutter may be an apparatus that can finely cut the gold thread twisted with four strands of gold rod into a length of about 3 cm to about 7 cm.

Since the gold thread cut in operation S260 and twisted with four strands of gold rod is twisted with the gold threads twisted with two strands of gold rods, the density difference between the both ends of the gold rod corresponding to each other in the direction orthogonal to the length direction of the gold thread twisted with four strands of gold rod is offset and thus the gold thread is not bent, thereby improving the flexibility due to the drawing of the gold rod. Thus, the productivity can be improved by removing a work process for straightening the gold thread twisted with four strands of gold rod. Also, since the gold thread can maintain the thread shape of 0.04 mm or less even if four strands of gold rod having a diameter of about 0.02 mm are spirally twisted, the gold thread can be applied to medical procedures and surgery.

When a user threads a needle with gold threads according to an embodiment and another embodiment of the present invention and performs a plastic (cosmetic) procedure or surgery, the surface area is wider than that of a thread having the same diameter and the frictional force with the skin is increased. Accordingly, the effect of the lifting procedure and surgery is increased. Also, it is possible to prevent side effects occurring in the body of a procedure or surgical subject.

In addition, since a gold thread having a diameter of 0.04 mm or less can be formed even if four strands of gold rods are twisted, the amount of gold used can be minimized, thereby reducing costs and improving economic efficiency. Also, since the gold threads formed by twisting a plurality of gold rods can maintain malleability, it is possible to obtain an effect of use that allows the procedure and surgery to proceed smoothly while preventing fracture.

Figure 7A:
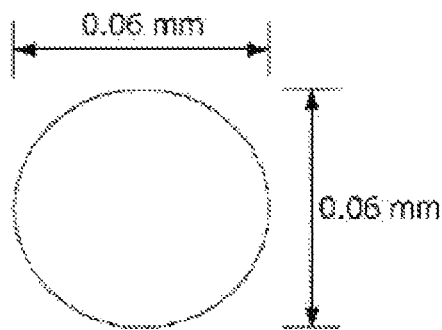
FIGS. 7A to 7B depict views illustrating a comparison of the skin contact area between a typical gold thread and a gold thread according to an embodiment of the present invention.
Figure 7B:
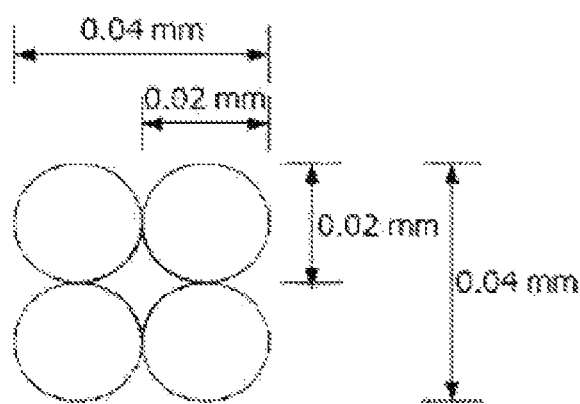

As shown in FIGS. 7A and 7B, the skin contact area of one strand of gold thread having a diameter of 0.06 mm is $0.06 \times \pi = 0.1884$, and the skin contact area of a gold thread twisted with four strands of gold rod having a diameter of 0.02 mm as described in the present disclosure is $0.02 \times \pi \times 4 = 0.2512$. Here, if $0.02 \times \pi = 0.0628$ that is the non-skin contact area on the inner surface of four strands of gold rod is subtracted from the skin contact area, the value is equal to 0.1884 mm That is, the skin contact area of one strand of gold thread having a diameter of 0.06 mm is the same as the skin contact area of a gold thread twisted with four strands of gold rod, but the amount of gold used can be reduced when the gold thread twisted with four strands of gold rod instead of one strand of gold thread is used. Accordingly, the effect of gold compared to the area is the same, but the amount of gold used can be reduced, thereby improving the economic efficiency.

A number of exemplary embodiments have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

LIST OF REFERENCE NUMERALS

100: gold thread
200: gold thread twisted with four strands of gold rod

What is claimed is:

1. A method of manufacturing a gold thread, the method comprising:
supplying a drawing material formed of gold to a die aperture;
passing the drawing material through the die aperture having a diameter of 0.02 mm or less;
forming a plurality of gold rods having the same diameter and shape as the die aperture;
winding at least two of the gold rods on at least two gold rod receiving rollers;
receiving the at least two gold rods wound on the at least two gold rod receiving rollers and twisting the at least two gold rods to form a gold thread;
winding the gold thread on a gold thread receiving roller; and
supplying the gold thread wound on the gold thread receiving roller to a cutter and cutting the gold thread into a certain length.

2. The method of claim 1, wherein the gold thread is obtained by twisting at least three gold rods.

3. A method of manufacturing a gold thread, the method comprising:
supplying a drawing material made of gold to a die aperture;
passing the drawing material through the die aperture having a diameter of 0.02 mm or less;
forming a plurality of gold rods, resulting from the passing of the drawing material, the gold rods having the same diameter and shape as the die aperture;
winding each of the plurality of gold rods on respective gold rod receiving rollers;
forming at least two first gold threads, wherein each of the first gold threads is formed by receiving at least two of the gold rods wound on the respective gold rod receiving rollers and twisting the two gold rods to form the first gold thread;
winding each of the first gold threads on respective first gold thread receiving rollers;
receiving the first gold threads wound on the respective first gold thread receiving rollers and twisting the two first gold threads to obtain a second gold thread;
winding the second gold thread on a second gold thread receiving roller; and
supplying the second gold thread wound on the second gold thread receiving roller to a cutter and cutting the second gold thread into a certain length.

* * * * *